United States Patent [19]

Klein

[11] Patent Number: 5,507,643
[45] Date of Patent: Apr. 16, 1996

[54] KIT, TOOL AND METHOD OF USE FOR SECURING A DENTAL RESTORATION ON A PREPARED TOOTH STUB

[75] Inventor: Philip B. Klein, Bryn Mawr, Pa.

[73] Assignee: Dental Logics, Inc., Bryn Mawr, Pa.

[21] Appl. No.: 310,911

[22] Filed: Sep. 22, 1994

Related U.S. Application Data

[63] Continuation-in-part of Ser. No. 212,623, Mar. 11, 1994, Pat. No. 5,453,010.

[51] Int. Cl.⁶ ..................................................... A61C 3/00
[52] U.S. Cl. ........................... 433/141; 433/220; 433/225
[58] Field of Search .................................. 433/220, 221, 433/225, 141, 163, 3

[56] References Cited

U.S. PATENT DOCUMENTS

| | | | |
|---|---|---|---|
| 1,397,067 | 11/1921 | Williams | 433/221 |
| 2,418,316 | 4/1947 | Reiter | 433/141 |
| 2,536,669 | 1/1951 | Thau-Jensen | 433/221 |
| 3,530,584 | 9/1970 | Karlström | 433/225 |
| 4,253,835 | 3/1981 | Ware | 433/220 |
| 4,382,784 | 5/1983 | Freller | 433/141 |
| 4,600,392 | 7/1986 | Weissman | 433/225 |
| 4,622,012 | 11/1986 | Smoler | 433/221 |
| 4,752,225 | 6/1988 | Bori | 433/221 |
| 4,778,388 | 10/1988 | Yuda et al. | 433/221 |
| 4,846,685 | 7/1989 | Martin | 433/221 |
| 4,850,874 | 7/1989 | Weissman | 433/225 |
| 4,934,936 | 6/1990 | Miller | 433/220 |
| 4,976,617 | 12/1990 | Carchidi | 433/141 |
| 5,073,112 | 12/1991 | Weil | 433/220 |
| 5,094,618 | 3/1992 | Sullivan | 433/221 |
| 5,161,973 | 11/1992 | Johnson | 433/221 |
| 5,290,171 | 3/1994 | Daftary et al. | 433/141 |

FOREIGN PATENT DOCUMENTS

| | | | |
|---|---|---|---|
| 312611 | 3/1956 | Switzerland | 433/221 |
| 1412768 | 7/1988 | U.S.S.R. | 433/141 |

Primary Examiner—Cary E. O'Connor
Attorney, Agent, or Firm—Caesar, Rivise, Bernstein, Cohen & Pokotilow, Ltd.

[57] ABSTRACT

A kit, a tool, and a method of use for securely retaining a dental restoration on a prepared tooth stub having a top surface and a bore extending therein. The kit comprises plural dental posts of varying sizes and a tool. Each dental post includes an enlarged head and a shank. The shank is an elongated member having a first longitudinal axis arranged to be fixedly secured within the stub's bore so that the post's enlarged head extends beyond the stub's top surface. The enlarged head has plural through passageways, e.g., a coronal passageway, and a transverse passageway that communicate with one another for receipt of a setable securement medium which flows therein and about the surface of the head to secure the dental restoration to the post. The tool includes a handle portion and an opposed pair of free end tips. Each free end tip is shaped to be inserted and frictionally received within the transverse passageway of selected ones of the dental posts of the kit to releasably mount the selected dental post on the tool. The tool's handle portion is arranged to be grasped in the hand of a user to carry the post to the prepared stub and to insert its shank into the bore so that its enlarged head is located above the top surface of the tooth stub. The tool can then be manipulated to release the frictional engagement between its free end tip and the dental post to enable the tool to be removed, leaving the dental post in place. The dental restoration can then be secured to the post's enlarged head.

13 Claims, 5 Drawing Sheets

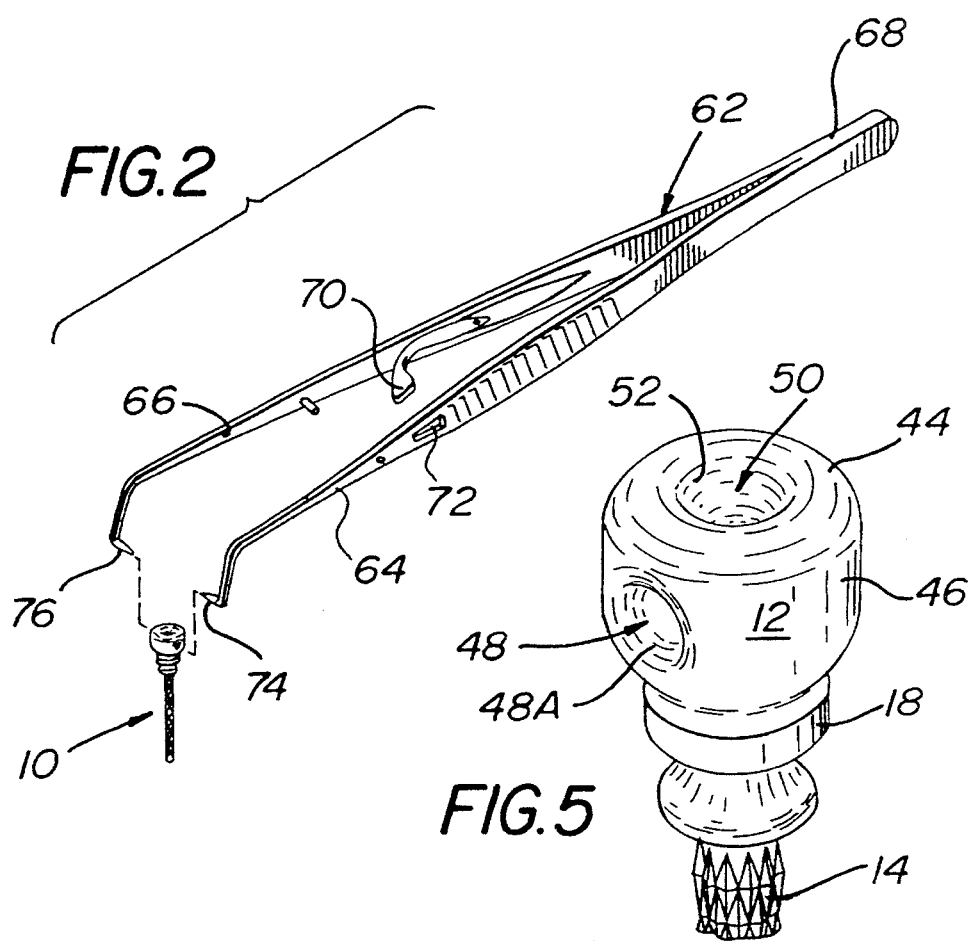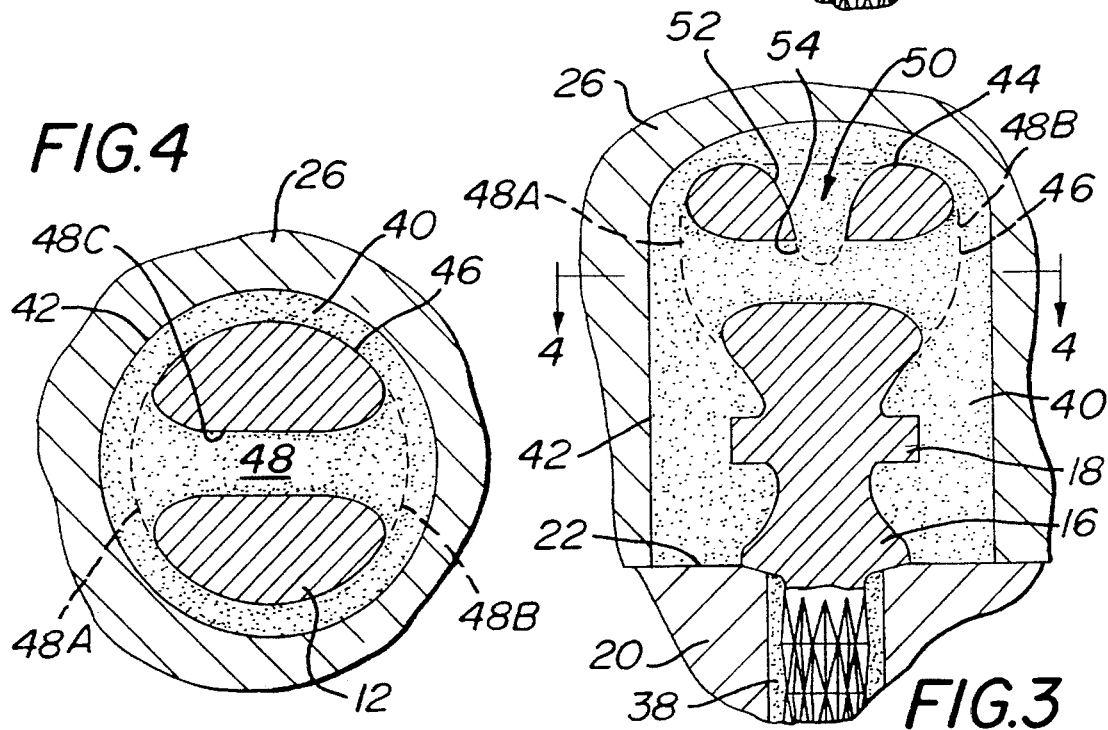

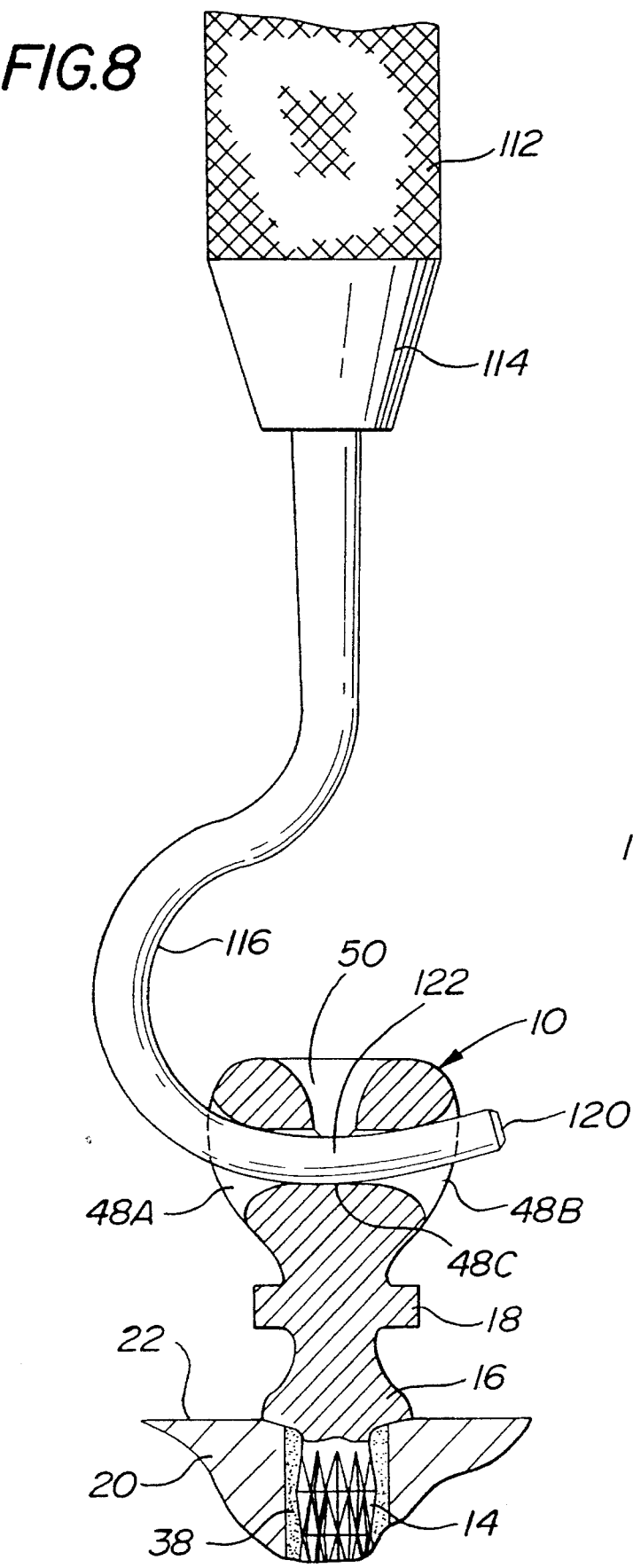
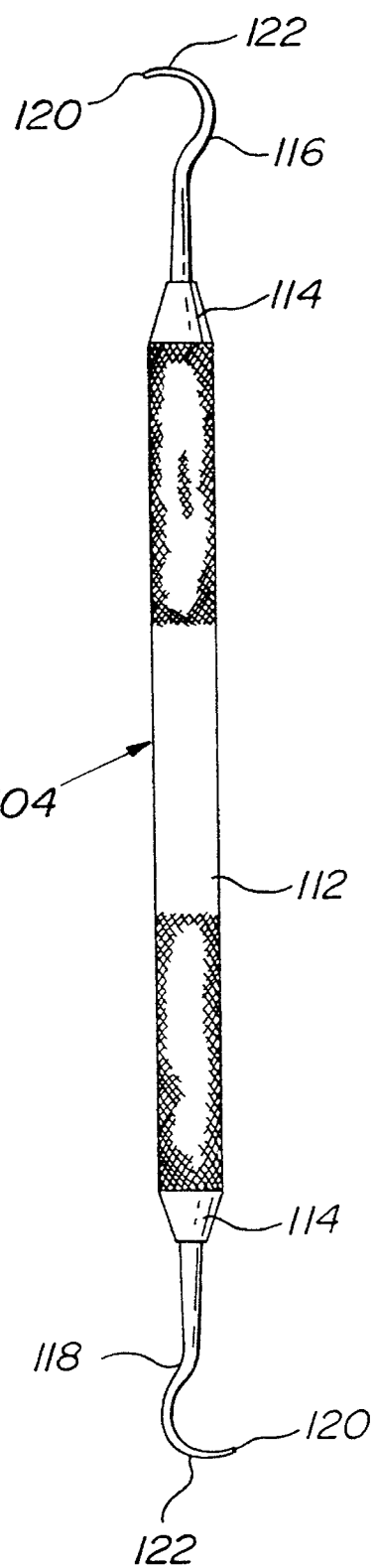

KIT, TOOL AND METHOD OF USE FOR SECURING A DENTAL RESTORATION ON A PREPARED TOOTH STUB

This application is a Continuation-In-Part of my earlier application Ser. No. 08/212,623, filed on Mar. 11, 1994, and entitled "Dental Post With Internal Retention Means", now U.S. Pat. No. 5,453,010, whose disclosure is incorporated by reference herein.

BACKGROUND OF THE INVENTION

The invention of this application relates particularly to kits, tools, and methods of use thereof. The kit includes at least one dental post and a tool used to hold dental post to carry it to the prepared tooth stub so that it can be mount on the prepared tooth stub to enable a dental restoration to be secured to the post thereafter.

It is well known in the field of dentistry to build up a dental restoration onto a tooth stub for replacement of missing dentition. The diseased or broken tooth is prepared leaving a tooth stub that provides a suitable support on which the restoration will be placed. After the root canal is cleaned and filled with the appropriate filling material it is partially reamed out to a proper size and depth forming a bore. A dental post is then selected and inserted into the prepared bore so that its shank substantially fills the bore while its head portion extends upwardly from the surface of the tooth stub. The post is retained within the bore using a suitable dental cement. Next, using a syringe or other dispensing means, a flowable dental core material is injected over the post head. The core material is formed and allowed to cure and harden on the post head to form a post-core buildup. Then, using a drill equipped with a high speed diamond burr, the post-core buildup is shaped to be fitted under a dental restoration, e.g., a porcelain or gold crown. Next, an impression is taken of the shaped post-core buildup which is used to fabricate the dental restoration. Finally, the dental restoration is fitted over the post-core buildup and cemented in place.

While numerous types of dental posts which are commercially available have provided improvements with respect to retention to and integration with core material, still further improvements were desirable. In my aforementioned patent application there is disclosed and claimed a dental post which provides significant advantages over the prior art to prevent accidental breaking off of the dental restoration after setting onto the dental post. The dental post of that application is arranged for securely retaining a dental restoration on a prepared tooth stub having a top surface and a bore extending therein and basically comprises an enlarged head and a shank. The shank is an elongated rod-like member having a first longitudinal axis, with the outside diameter of the shank measured along a second axis perpendicular to the first axis and being a predetermined dimension. The shank is arranged to be fixedly secured within the bore so that the enlarged head extends beyond the top surface of the prepared tooth stub. The enlarged head has an outside diameter measured along a third axis parallel to the second axis and is a predetermined dimension. The enlarged head has plural through passageways, e.g., a coronal passageway, and a transverse passageway that communicate with one another.

The plural through passageways are arranged for receipt of a setable securement medium which flows therein and about the surface of the head to secure the dental restoration to the post.

A dental pliers is also disclosed in the application for the safe handling and insertion of the dental post into the prepared tooth. While the dental pliers of that application is suitable for its intended purposes, it never the less leaves something to be desired from the standpoints of simplicity of construction and ease of use, e.g., ease of transporting the dental post to the prepared tooth stub while releasably supporting the post so that its shank can be readily inserted within the bore in the stub to secure the dental post in place, and for simple manipulation to release the tool from the post. A need thus exists for tool to better achieve those ends.

OBJECTS OF THE INVENTION

Accordingly, it is a general object of the present invention to provide a kit comprising at least one dental post and a tool for transporting and mounting the dental post onto a prepared tooth stub which addresses that need.

It is another object of this invention to provide a kit comprising at least one dental post constructed in accordance with my aforementioned patent application and a tool for transporting and mounting that dental post onto a prepared tooth stub.

It is still another object of this invention to provide a tool for releasably mounting a dental post thereto so that the dental post can be readily carried to a prepared tooth stub and inserted therein, whereupon the tool can be readily manipulated to release the dental post from the tool leaving the dental post in place.

It is yet another object of this invention to provide a method for releasably mounting a dental post onto a tool, using the tool to carry the dental post to a prepared tooth stub so that the post's shank can be inserted within a bore in the tooth stub, and thereafter manipulating the tool to release it from the dental post to leave the dental post in place in the tooth stub, whereupon a dental restoration can be secured thereto.

SUMMARY OF THE INVENTION

These and other objects of this invention are achieved by providing a kit, a tool and a method of use for securing a dental restoration on a prepared tooth stub having a top surface and a bore extending therein.

The kit basically comprises at least one dental post and a tool. In accordance with an exemplary embodiment of the invention to be described later, the kit comprises plural dental posts of various sizes, the tool, and plural drill bits of various sizes for drilling a bore in a tooth stub to accommodate a selected one of the various sized posts, all housed within a box or case.

The dental post comprises an enlarged head and shank having a longitudinal axis. The shank is arranged to be located within the bore of the tooth stub. The enlarged head of the dental post has a passageway extending fully therethrough perpendicular to its longitudinal axis. The passageway has an opposed pair of open, e.g., funnel-shaped, ends.

The tool is arranged for the safe handling and insertion of the shank of the dental post into the bore of the prepared tooth stub. To that end the tool basically comprises a handle portion and at least one free end tip. The free end tip is shaped, e.g., is arcuate and includes a portion of a predetermined outer diameter, to be inserted and frictionally received within the passageway in the post's enlarged head from either of the opposed pair of open ends of the passageway to releasably mount the dental post on the tool. In the exemplary embodiment the tool includes a pair of free end tips, one larger than the other to handle a large sized post.

The handle portion of the tool is arranged to be readily grasped in the hand of a user so that a desired dental post can be retrieved from the kit, e.g., from the box containing the plural posts of differing sizes, and then to carry the selected dental post to the prepared tooth stub and to insert the shank of the selected dental post into the bore in the tooth stub so that the post's enlarged head is located above the top surface of the tooth stub. Once this is accomplished the tool is readily manipulated to release the frictional engagement between the tool's free end tip and the dental post to enable the tool to be removed therefrom, leaving the dental post in place.

A dental restoration can then be secured, e.g., adhesively affixed, to the enlarged head of the dental post projecting above the top surface of the tooth stub.

BRIEF DESCRIPTION OF THE DRAWINGS

Other objects and many attendant features of this invention will become readily appreciated as the same becomes better understood by reference to the following detailed description when considered in connection with the accompanying drawing wherein:

FIG. 2 is an isometric view of the dental post of FIG. 1 shown for releasable grasping by a pair of jaws of a tool in the form of a dental pliers;

FIG. 3 is an enlarged sectional view taken along lines 3—3 of FIG. 1;

FIG. 4 is an enlarged sectional view taken along lines 4—4 of FIG. 3;

FIG. 5 is an enlarged isometric view of the enlarged head of the dental post of FIG. 1;

FIG. 8 is an enlarged isometric view of the dental post of FIG. 1 shown releasable frictional secured to the pronged tip of the tool shown in FIG. 7 during the insertion of the shank of the dental post into a bore in the prepared tooth stub; and FIG. 9 is an enlarged plan view of the tool shown in FIG. 7.

DETAILED DESCRIPTION OF THE PREFERRED EMBODIMENT

Figure 1:
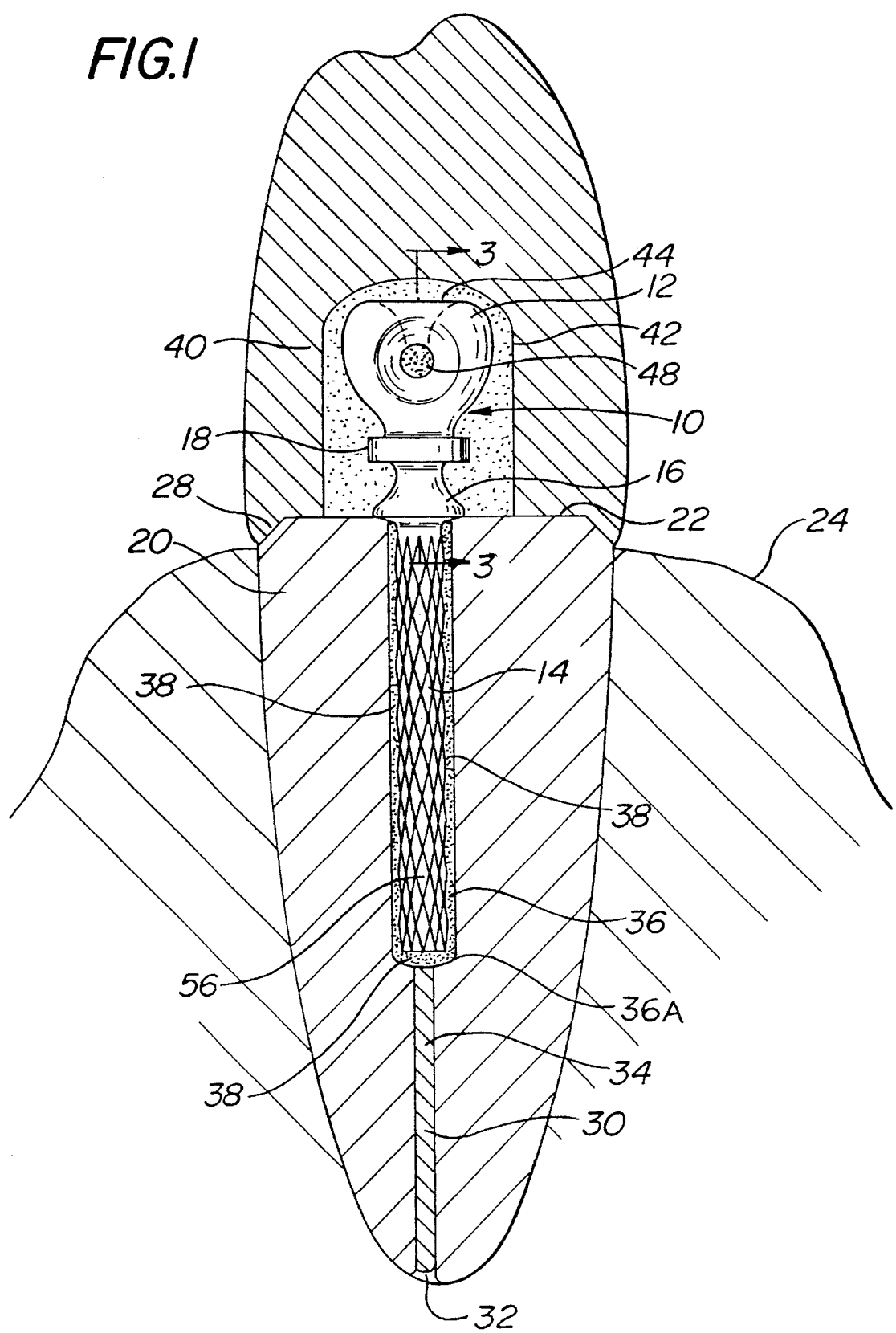
FIG. 1 is a sectional view of a finished dental restoration showing a prepared tooth stub and crown with the dental post of the kit of the present invention shown in full retained within the tooth stub using dental cement.

Referring now to the various figures of the drawings where like reference numerals refer to like parts, in FIG. 1 there is shown a dental post 10, constructed in accordance with this invention. The details of the dental post 10 will be described later. Suffice it for now to state that the dental post of the present invention is arranged to be inserted and retained within the root canal of an existing tooth stub to facilitate the build up of a dental restoration onto the tooth stub.

Referring to FIGS. 1, 3, 4 and 5, one exemplary embodiment of the dental post of the present invention is shown generally as 10 and comprises an enlarged or bulbous head 12 an elongated shank 14, a shoulder 16 and a strengthening flange 18. Although separately identified, the bulbous head, elongated shank, shoulder and strengthening flange are integrally connected and formed as a unitary structure. The dental post of the present invention is comprised of any suitable material, e.g., bio-compatible, machinable stainless steel.

Prior to the insertion of the dental post 10 into the tooth stub 20 as shown in FIG. 1, a suitable upper surface 22 somewhat above the gum-line 24 is prepared to support a fitted dental restoration 26. Many times, the outer edge of the upper surface 22 is shaped to form a bevel 28 to facilitate attachment of the dental restoration 26. The particular tooth stub illustrated in FIG. 1 has a single root canal 30 extending downward to an apical opening 32. In order to retain the dental restoration 26 onto the tooth stub 20, there is required a dental post such as one of the present invention.

Prior to the placement of a dental post in the tooth root, the root canal 30 will be endodontically prepared in a manner well known to those skilled in the art through the use of endodontic files (not shown) to enlarge the root canal 30 by removing pulp material therefrom. The entire length of the root canal 30 is sealed with a suitable sealant 34, such as gutta percha. Next, drill bits (to be described later with reference to the kit shown in FIG. 7) of successively larger sizes are utilized to enlarge the upper portion of the prepared root canal opening to form a dental post space or bore 36. The dental post space or bore 36 is comprised of a cylindrically shaped sidewall 36A that is enlarged to a diameter appropriate to receive the shank portion 14 of the dental post 10. Typically, the dental post space 36 extends approximately fifty to sixty (60) percent of the depth of the prepared tooth stub 20. The dental post space 36 provides a suitable receptacle for the dental post 10 which helps anchor the tooth restoration, i.e., crown 26. The prepared root canal 30 below the dental post space 36 and extending down to the apical opening 32 remains sealed with gutta percha 34.

A dental post 10 is then selected and inserted into dental post space 36 so that shank 14 substantially fills the dental post space 36. Once shank 14 is inserted, there should be adequate space around it so that cement 38 employed in this technique can flow in the annular space between the shank 14 and the wall 36A of dental post space 36 without creating hydraulic stresses. The post shank 14 is retained within the dental post space 36 using a suitable dental cement 38. After insertion of shank 14, the bulbous head 12 extends upwardly from the top surface 22 of the tooth stub 20. Using a syringe (not shown), a flowable setable dental core material 40 is injected over the bulbous head 12 and through a plurality of through openings contained therein. These plural openings will be described in further detail below. Once the core material 40 has set and hardened over the dental post 10, a structure is formed known as a post-core buildup 42. Next, using a drill equipped with a high speed diamond burr (not shown), the post-core buildup 42 is shaped to be fitted with the dental restoration 26. Next, an impression (not shown) is taken of the shaped post-core buildup 42 from which a dental restoration 26, such as a porcelain or gold crown is fabricated. Finally, the dental restoration 26 is fitted and cemented in place over the post-core buildup 42.

The bulbous head 12 of the dental post 10 is formed by any suitable means, e.g., stamping or swaging. The bulbous head 12 is provided in various outside diameter head sizes. That is, the dentist is able to select the appropriate head size based upon the amount of space available above the top surface 22 of tooth stub 20 for mounting dental restoration 26. For example, where a smaller tooth is being prepared for a crown and the amount of space on which to form a post-core buildup 42 is severely limited, it is necessary for the dentist to select a dental post 10 having a relatively small bulbous head 12 so that a sufficient amount of core material 40 can be formed thereover to build a strong post-core buildup 42. In such cases, it is necessary for the dentist to select a dental post 10 of the present invention having a relatively small bulbous head 12. In other instances, where there is little tooth structure above top surface 22 a dental post having a larger bulbous head is appropriate.

As shown in FIGS. 3, 4 and 5, the bulbous head 12 is comprised of a flat coronal surface 44, a sidewall 46, a transverse opening 48, a coronal opening 50 and a coronal rest seat 52. In FIG. 4, the sidewall 46 is shown as being generally circular and therefore having a diameter extending perpendicular to its longitudinal central axis of the post 10. The transverse opening 48 is an open passageway that extends diametrically through sidewall 46 perpendicular to the longitudinal central axis. As shown in FIGS. 1 and 5, transverse opening 48 is a circular through passageway and is located concentrically about the diameter of sidewall 46. As shown in FIGS. 3, 4 and 5, the transverse opening 48 is flared or chamfered at ends 48A and 48B. By providing flared or chamfered ends, 48A and 48B an increased volume of core material 40 can flow into transverse opening 48 in order to form a stronger post-core buildup. Additionally, flared ends 48A and 48B provide an escape route for trapped air within transverse opening 48. In accordance with one preferred embodiment of this invention the inner diameter of the smallest portion of the opening 48, i.e., the portion 48C (FIG. 4) between the flared ends 48A and 48B, is approximately 0.22 inch (0.56 mm) and in another preferred embodiment is approximately 0.32 inch (0.81 mm).

The coronal opening 50 is an open passageway that extends downwardly from the coronal surface 44 and communicates with transverse opening 48 at an interface shown by phantom line 54 (FIG. 3). The coronal opening 50 is generally circular along its length and is concentric with the post axis (i.e., the central longitudinal axis). As the coronal opening 50 extends upward from transverse opening 48 toward coronal surface 44 it widens to form a coronal rest seat 52. The coronal rest seat 52 is cup-shaped and allows for an increased volume of core material 40 to flow into the coronal opening 50 to provide added stability and strength to the post-core buildup.

Although coronal opening 50 is illustrated in FIG. 3 as extending from coronal surface 44 to transverse opening 48, it should be understood that in accordance with an alternative embodiment of the present invention, the coronal opening 50 can extend from the coronal surface 44, through transverse opening 48 and extend further for a predetermined distance along the post axis through post shank 14 to provide increased volume into which core material 40 can flow to provide added stability and strength.

In addition, as shown in FIG. 1, in an alternative embodiment of the present invention, there is provided a shoulder 16 located above shank 14. In this embodiment, when dental post 10 is inserted in dental post space 36, the shoulder 16 abuts the upper surface 22 of the tooth stub 20. The shoulder 16 serves to dissipate lateral and occlusal, i.e., downward, forces away from tooth root 30, thereby preventing root fracture during chewing.

In accordance with the present invention, the dental post 10 is provided to the dental practitioner with a shank 14 of predetermined length that corresponds to respective drill sizes used in creating dental post space 36.

The shank 14 of the dental post is cylindrical in shape, having a constant cross-sectional diameter along its entire length.

According to the present invention, dental posts will be provided to the dentist in a variety of shank diameters, e.g., from 0.036 to 0.060 inches (0.914 to 1.524 mm) in diameter to assure a snug fit within variously sized dental post spaces 36, both narrow and wide. If the dental post space is relatively wide, a post containing a comparatively thick shank is selected for insertion therein. Conversely, if the dental post space 36 is narrow, a post containing a comparatively narrow shank is selected for insertion therein.

During chewing, the portion of dental post 10 extending above shoulder 16 is exposed to significant lateral forces. Where shank 14 is comparatively small in diameter, e.g., 0.036 to 0.040 inches (0.914 to 1.016 mm), these lateral forces can bend and break post 10 at any narrow point above shoulder 16. To provide reinforcement strength and thickness to the narrowest portion of dental post 10 extending above upper surface 22, the strengthening flange 18 is interposed between bulbous head 12 and shoulder 16. It should be understood that strengthening flange 18 is only necessary where shank 14 is comparatively small in diameter, e.g., 0.036 to 0.040 inches (0.914 to 1.016 mm). Where a dental post 10, constructed in accordance with this invention is comprised of a shank 14 having a larger diameter, e.g., 0.045 inches (1.143 mm) or larger the strengthening flange 18 is not necessary.

In the preferred embodiment of the present invention, the entire exterior surface of the shank 14 is comprised of a multitude of small planar facets 56 angularly oriented with respect to each other. By utilizing multiple angular facets 56, the surface area over the entire exterior surface of the shank 14 is maximized to provide superior bonding ability with cement upon insertion into the root canal. In this preferred embodiment, because the shank 14 is not threaded, it will not cut into dentin along the post space sidewall 36A, and will therefore avoid the risk of fracturing the tooth root during insertion. The multiple angular facets 56 can be provided along the exterior surface of the shank by a variety of methods, e.g., embossing.

Figure 6:
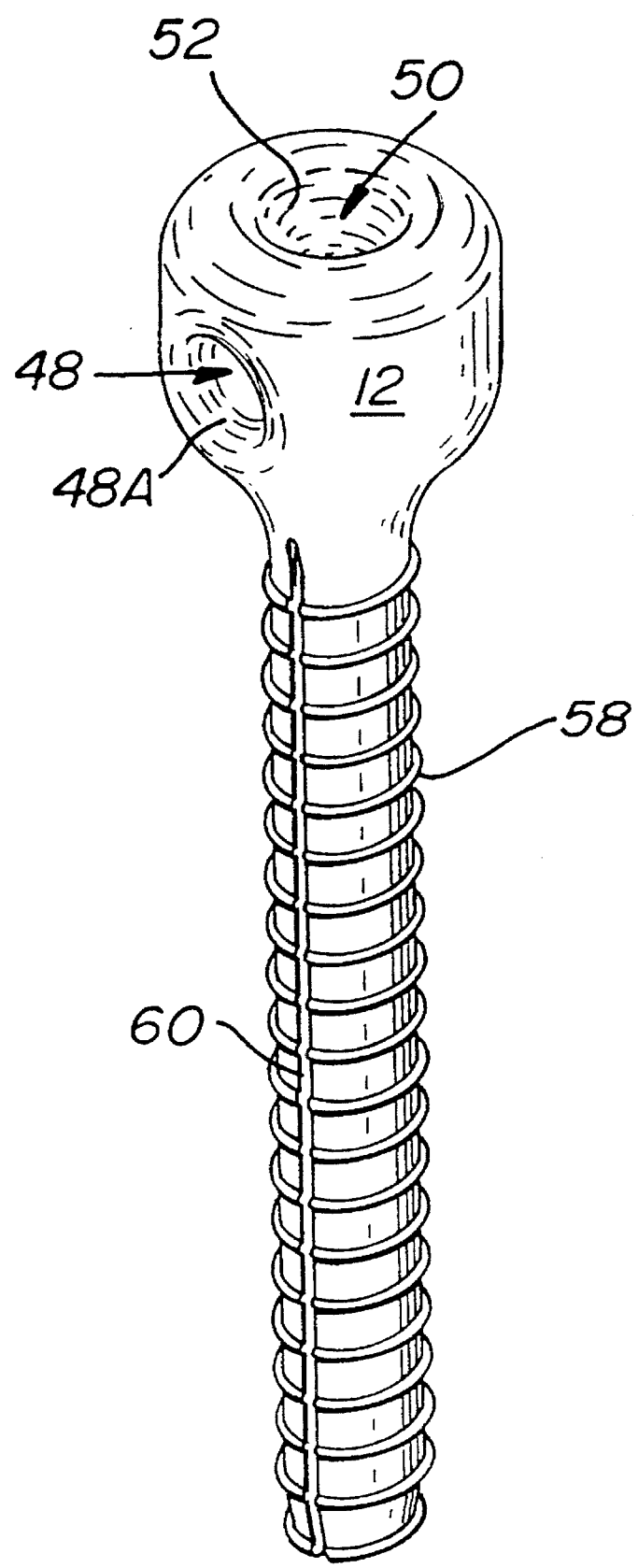
FIG. 6 is an enlarged isometric view of an alternative embodiment of a post forming a portion of the kit of the present invention.

Referring to FIG. 6, in an alternative embodiment of the present invention, shank 14 is provided with a continuous helical thread 58 and flute 60. The thread 58 is formed about the surface of shank 14 and extends over its entire length. The helical thread 58 has a very small pitch so as to maximize the number of revolutions the thread winds around shank 14. After application and cure of dental cement 38 between helical thread 58 and post space sidewall 36A, the shank 14 is securely anchored within the dental post space 36. This embodiment, utilizing a continuous helical thread 58 is less expensive to manufacture than the shank comprising multiple angular facets previously described in the preferred embodiment. The flute 60 extends longitudinally for a substantial length over shank 14 and serves to vent air, liquids or cement in the root canal during the insertion and seating of shank 14. The flute 60 also eliminates undesired pressure build-up and risk of tooth root fracture during insertion of shank 14. Although not shown in FIG. 6 the shoulder 16 and/or the strengthening flange 18 could be incorporated in this embodiment in accordance with this invention.

In FIG. 2, there is shown a hand-held dental pliers 62 modified in accordance with another aspect of this invention for safe handling and insertion of the dental post 10 of the present invention. Such hand-held dental pliers 62 are similar in construction and operation to dental pliers sold by various dental instrument retailers including the Henry Schein Company. Such hand-held pliers are comprised of a pair of arms 64 and 66 joined at one end to form a proximal handle 68. In accordance with this invention at the opposite end of each arm is a projection (to be described later) to enable the lifting of the dental post 10. In addition the hand-held pliers 62 are provided with a locking arm 70 and catch 72 to enable the practitioner to hold dental post 10 between arms 64 and 66 without applying pressure with thumb and forefinger.

As mentioned earlier the distal end of each arm 64 and 66 is provided with a pair of projections. These are designated by the reference numbers 74 and 76. The projections 74 and 76 are diametrically opposed and facing inwardly. The projections are conically shaped to fit within the flared ends 48A and 48B of transverse opening 48 to enable a dental practitioner to pick up and insert dental post 10 into dental post space 36 of prepared tooth stub 20.

In particular, to pick up dental post 10 using dental pliers 62 in accordance with this aspect of the present invention, the dental practitioner aligns projections 74 and 76 of dental pliers 62 with the flared ends 48A and 48B of transverse opening 48 and squeezes arms 64 and 66 with thumb and forefinger so that projections 74 and 76 enter flared ends 48A and 48B of transverse opening 48. Further squeezing will cause locking arm 70 to enter catch 72 to securely engage dental post 10 in dental pliers 62. With dental post 10 securely held in place between arms 74 and 76, the risk of losing grip of the dental post 10 during insertion into the dental post space 36 is greatly reduced.

Figure 7:
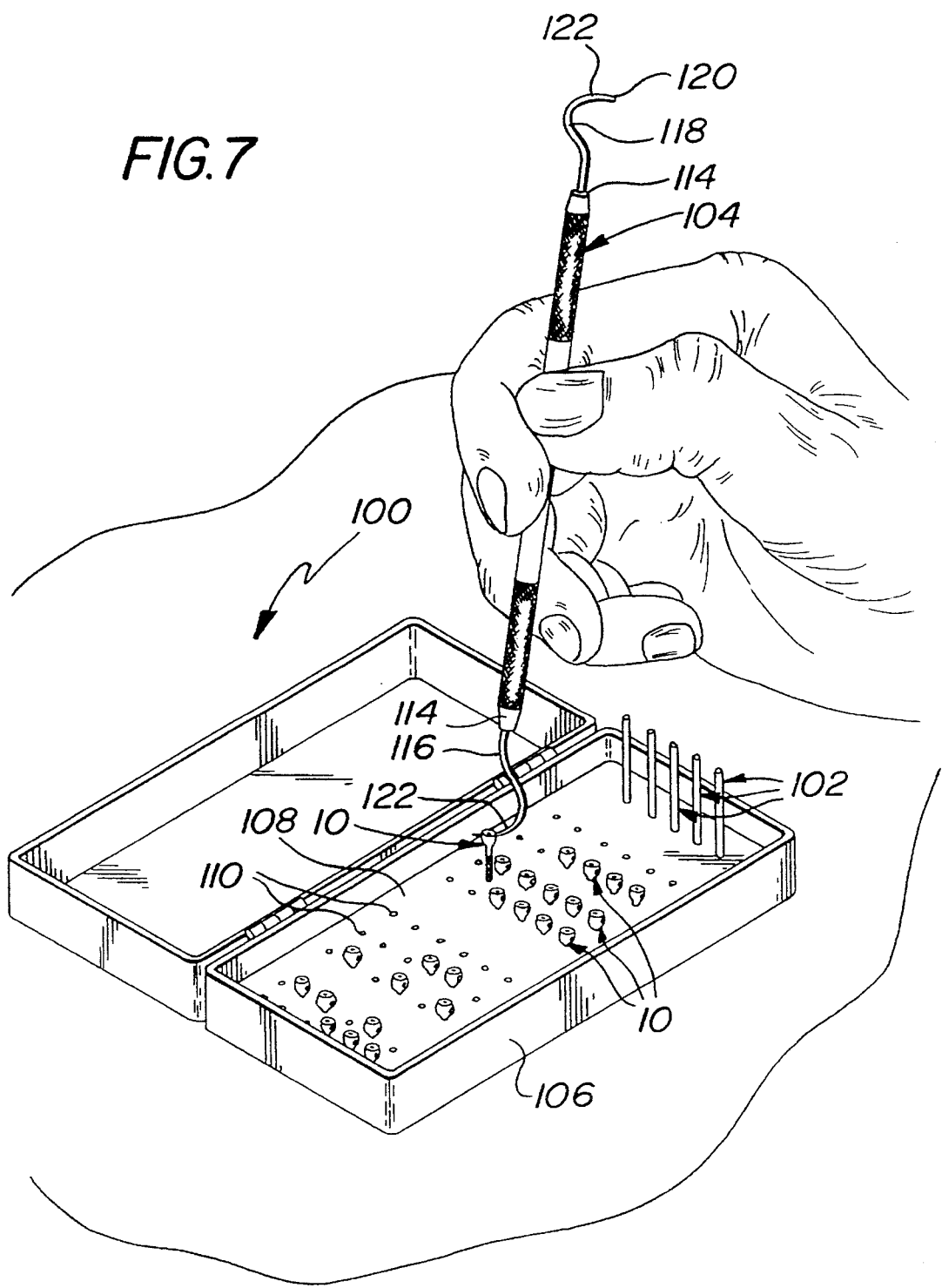
FIG. 7 is an isometric view of a kit constructed in accordance with this invention shown with a user, e.g., a dentist, in the process of picking up a selected post by another tool constructed in accordance with this invention to carry the dental post to a prepared tooth stub.

Referring now to FIG. 7 a dental kit 100 constructed in accordance with one aspect of this invention is shown. The kit basically comprises a plurality of dental drills 102, a plurality of posts 10, and a tool 104. The drills and posts are all housed within a clamshell-type hinged box 106. The box 106 includes an insert 108 having a plurality of recesses 110 therein, each of which is arranged to receive a respective one of the drills 102 or posts 10 to hold it directed upward, e.g., either vertically (as shown in FIG. 7) or at an acute angle, so that any drill 102 and/or post 10 can be readily retrieved therefrom by the dentist when that drill and/or post is needed.

In accordance with a preferred aspect of this invention all of the posts are constructed in accordance with the teachings of this application and its parent application, with the only differences among the posts 10 being the size of their shanks and/or enlarged heads and openings 48 therein. The various sized posts are provided in the kit so that the dentist can select an appropriately sized post for the dental restoration to be made. The drills 102 are all of generally conventional construction and are in various sizes to create a desired size space or bore 36 in the root 30 of the tooth to be reconstructed. The tool 104 is provided to enable the dentist to readily pick-up or retrieve the selected post 10 from the kit, to carry the selected post to the prepared tooth stub, to facilitate the insertion of the selected post's shank into the bore in the tooth stub, and to then release the post therefrom so that the tool can be withdrawn.

The details of the tool 104 can best be seen in FIG. 9. As can be seen therein the tool basically comprises an elongated cylindrical handle portion 112 having a pair of ends 114. The outer surface of the handle portion is knurled adjacent each end 114 to facilitate the grasping of the instrument in the hand of a user, e.g., dentist, like shown in FIG. 7. An arcuate, e.g., "C-shaped", tip 116 projects from one of the ends 114, while a similar tip 118 projects from the other of the ends 114. The tips 116 and 118 serve as the means for picking up, transporting and placing the posts 10 in the tooth stub. To that end, each tip 116 and 118 is of circular cross section and tapers downward to a chamfered free end 120 (FIG. 8). The tips 116 and 118 are oriented so that the free end 120 of tip 116 extends in one direction generally perpendicular to the longitudinal axis of the handle 112, while the free end 120 of the tip 118 extends in the opposite direction. The tapering cross sectional area of the tip 116 is smaller than the corresponding cross sectional area of the tip 118 so that the middle portion 122 of the tip 116 can fit within and frictionally engage the 0.022 inch (0.06 cm) passageway portion 48C of the posts 10 of the kit having that sized transverse passageway 48, as shown in FIG. 8. The middle portion 122 of the tip 118 is arranged to fit within and frictionally engage the 0.032 inch (0.08 cm) passageway portion 48C of the posts 10 of the kit having that larger sized transverse passageway.

The use of the kit 100 will now be discussed assuming that the dentist has completed the root canal therapy and has decided that the tooth requires the use of a dental post 10 in order to build up the tooth for a crown or restoration 26. To that end, the dentist selects appropriately sized drills 102 from the kit 100 and uses them in the same manner as described heretofore to remove the root canal filling material and shape the root canal into a desired sized space or bore 36 so that it can receive the shank 14 of an appropriately sized dental post 10 in the kit. Once the bore 36 has been prepared to the proper length and diameter, the dentist selects from the kit the post 10 that most closely corresponds to the length and diameter of the prepared space or bore 36. The removal of the selected post 10 from the insert 108 in the box 106 is achieved by inserting either the tip 116 or 118 (depending upon the size of the passageway 48 in the selected post) of the tool 104 through the transverse passageway 48 in the head of the desired post from either opening 48A or 48B until the outer surface of the middle portion 122 of the tip firmly engages the inner surface of the central portion 48C of the passageway. The frictional engagement between the outer surface of the tool's tip portion 122 and the inner surface of the post's passageway portion 48C effectively releasably secures the selected post to the tool. This action allows the dentist to adeptly lift the post out of the box of the kit as shown in FIG. 7 and to safely and securely carry the post to the patient's prepared tooth, e.g., the stub 20.

By holding the handle 112 of the tool 104 with the post 10 engaged on its tip 116/118 the dentist can then carefully direct the post's shank 14 into the post bore land to seat the post for the initial "try-in" as shown in FIG. 8. At this point the dentist determines whether any adjustments are necessary to the post shank. After the try-in the dentist can simply pull the post out of the post channel keeping the tool tip engaged within the transverse passageway 48 in the post head throughout the procedure. This gives the dentist total control of an otherwise difficult maneuver (as it is easy to "lose" or drop a post picked up with conventional dental pliers/tweezers and is also difficult to retrieve a post after try-in with such conventional tools).

Once the post length has been adjusted, if necessary, the post is ready to be cemented into the root permanently. To that end the dentist holds the handle of the tool 104 with its tip extending through and frictionally engaging the transverse passageway 48 in the post. The dentist then directs the post shank across a pool of dental cement (not shown) on a mixing pad (not shown). It should be noted that the portion of the tip extending through the transverse passageway 48 serves to block out cement from gaining ingress into the transverse passageway 48 during the cementation procedure.

Once the post's shank is fully lined with dental cement, the dentist utilizes the tool 104 to carry and direct the dental post's shank into the prepared root bore to complete the insertion and final cementation of the post. In particular, once the post is inserted into the canal or bore the dentist turns the tool 104 a quarter (¼) turn back and forth about the axis of the passageway 48, essentially oscillating the tip within the post head. This oscillating movement, along with a lateral pull on the tool in a direction parallel to that axis and away from the post, releases the tip from within the transverse passageway 48. The tool 104 can then be readily removed or retracted completely out of the passageway 48, leaving the post 10 permanently cemented into the root. The flowable setable dental core material 40 is then injected over the enlarged head 12 and through the openings and passageways 48 and 50 so that a post core build-up can be formed and the crown ultimately adhesively secured thereto, as described earlier.

As should be appreciated from the foregoing the kit 100 of the subject invention provides the dentist with a complete integrated system for use in making a dental restoration. Thus, the kit includes various sized drills for preparing a tooth for reconstruction by producing a desired size bore in the root of the tooth, various sized posts corresponding to the drill sizes and having different sized bulbous or enlarged heads appropriate for the amount of tooth structure available and which are easy to use and effective for securing a dental restoration to the prepared tooth stub, and a tool for effectively transporting and supporting the selected post and for manipulating it during its securement to the prepared tooth stub.

It should be pointed out at this juncture that, like stated in my aforementioned patent application, the enlarged head of the dental post of this kit may be of shapes other than "bulbous", e.g., cubic, so long as it includes at least one transverse passageway as described heretofore for enabling it to be picked up and manipulated by tools and for enabling the flowable setable dental core material to securely adhere thereto so that an effective post core build-up can be fabricated therefrom and to which a crown can be adhesively secured. The transverse passageway need not include tapered entrances 48A and 48B if desired, e.g., the transverse passageway can be of uniform cross sectional area throughout its length, and can be of any shape, e.g., round, square, triangular, etc. Moreover, the passageway 50 may not be needed to create a coronal seat.

Without further elaboration the foregoing will so fully illustrate my invention that others may, by applying current or future knowledge, adapt the same for use under various conditions of service.

I claim:

1. A kit for securing a dental restoration on a prepared tooth stub having a top surface and a bore extending therein, said kit comprising at least one dental post and a tool, said dental post comprising an enlarged head and shank having a longitudinal axis, said shank being arranged to be located within the bore of the tooth stub, said enlarged head having a passageway extending fully therethrough perpendicular to said longitudinal axis, said passageway having an opposed pair of open ends, said tool being arranged for the safe handling and insertion of said shank of said dental post into the bore of the tooth stub and comprising a handle portion and a free end tip, said free end tip being shaped to be inserted and frictionally received within said passageway from either of said opposed pair of open ends to releasably mount said dental post on said tool, said handle portion being arranged to be grasped in the hand of a user to carry said shank of said dental post into the bore in the tooth stub so that said enlarged head is located above the top surface of the tooth stub, whereupon said tool can be manipulated to release the frictional engagement between said free end tip and said dental post to enable said tool to be removed therefrom, leaving said dental post in place, whereupon a dental restoration can be secured to said enlarged head of said dental post.

2. The kit of claim 1 wherein each of said open ends of said passageway in dental post is funnel-shaped.

3. The kit of claim 2 wherein said dental post comprises an opening in said enlarged head concentric with said longitudinal axis and in communication with said passageway for receipt of a setable securement medium therein to form a coronal seat for said dental restoration.

4. The kit of claim 1 wherein said dental post comprises an opening in said enlarged head concentric with said longitudinal axis and in communication with said passageway for receipt of a setable securement medium therein to form a coronal seat for said dental restoration.

5. The kit of claim 1 wherein said free end tip is arcuate in shape.

6. The kit of claim 5 wherein a portion of said arcuate free end tip is of circular cross section and of an outside diameter approximately the same as the inside diameter of the passageway in the enlarged head of the dental post.

7. The kit of claim 1 wherein said handle portion of said tool is elongated and has a pair of ends, with each of said ends having an arcuate free end tip located thereat, and with a portion of one of said arcuate free end tips having a larger outside diameter than the corresponding portion of the other of said free end tips.

8. A tool for the safe handling and insertion of a dental post into a bore in a prepared tooth stub for securing a dental restoration to the post, the dental post comprises an enlarged head and shank with the shank having a longitudinal axis and with the enlarged head having a passageway extending fully therethrough perpendicular to the longitudinal axis, the passageway having a portion of a first internal diameter, said tool comprising a handle and a pair of arcuate tips, said handle being an elongated member having a pair of opposed ends, each of said ends having having a respective one of said pair of arcuate tips located thereat, each of said arcuate tips including a portion of circular cross section having an outer diameter approximately the same as the first inner diameter of the passageway in the dental post, with the outer diameter of a portion of one of said arcuate tips being greater than the outer diameter of a corresponding portion of the other of said arcuate tips, each of said arcuate tips being arranged to be inserted within the passageway in the dental post so that said portion of circular cross section releasably frictionally engages the portion of the post's passageway having the first internal diameter, whereupon said tool can be used to carry the dental post to the prepared tooth and to insert the shank of the dental post into the bore in the tooth stub so that the post's enlarged head is located above the top surface of the tooth stub, and then said tool can be manipulated to release the frictional engagement between the tool and the post to enable said tool to be removed from the dental post and the tooth stub, leaving the dental post in place.

9. A method for securing a dental restoration on a prepared tooth stub having a top surface and a bore extending therein, said method comprising the steps of:

(a) providing at least one dental post and a tool, the dental post comprising an enlarged head and shank having a longitudinal axis, the enlarged head having a passageway extending fully therethrough perpendicular to the longitudinal axis of the shank of the dental post, said passageway having an opposed pair of open ends, the tool comprising a handle portion and a free end tip, the free end tip being shaped to be inserted and frictionally received within the passageway, (b) grasping the handle of the tool and manipulating it so that the tool's free end tip is inserted into the passageway from either of the ends of the passageway to frictionally engage the passageway and thereby releasably mount the dental post on the tool, (c) carrying the tool and the dental post releasably mounted thereon to the prepared tooth stub, to insert the shank of the dental post within the bore in the tooth stub, and (d) manipulating the tool to release the frictional engagement between the tool and the post, and then withdrawing the tip of the tool from the passageway in the post to leave the post in place with respect to the tooth stub, whereupon the post is ready to have a dental restoration secured thereto.

10. The method of claim 9 wherein said at least one dental post and tool is provided as a part of a kit, said kit having plural dental posts of varying sizes.

11. The method of claim 9 wherein the passageway in the dental post is of circular cross section and has a first inner diameter, and wherein the free end tip of the tool is arcuate and includes a portion of circular cross section and having an outer diameter approximately the same as the inner diameter of the passageway of the dental post.

12. The method of claim 9 wherein the passageway in the dental post is of circular cross section and has a first inner diameter, and wherein the handle of the tool is an elongated member having a pair of opposed ends, with each of said ends having a respective free end tip located thereat, and with the outer diameter of a portion of one of said tips being greater than the outer diameter of a corresponding portion of the other of said tips, whereupon one of said tips can be received within the passageway in one size dental post of the kit and the other of the arcuate tips can be received within the passageway in a larger size dental post of the kit.

13. The method of claim 9 additionally comprising the step of providing a flowable setable dental core material so that it flows into and through said passageway to set up so that it is permanently secured to said enlarged head of said post to enable a post-core buildup to be formed thereby.

* * * * *